United States Patent [19]
Ambrosio et al.

[11] Patent Number: 5,243,970
[45] Date of Patent: Sep. 14, 1993

[54] DOSING DEVICE FOR ADMINISTERING METERED AMOUNTS OF POWDERED MEDICAMENTS TO PATIENTS

[75] Inventors: Thomas J. Ambrosio, Somerville; Indradat Jagnandan, West Orange; Henry R. Sochon, Clifton; Srinivas Manthena, Bloomfield; William S. Blake, Linwood, all of N.J.

[73] Assignee: Schering Corporation, Kenilworth, N.J.

[21] Appl. No.: 685,803

[22] Filed: Apr. 15, 1991

[51] Int. Cl.⁵ .................. A61M 15/00; A61M 16/00; B05D 7/14; B65D 83/06
[52] U.S. Cl. .......................... 128/203.15; 128/203.12
[58] Field of Search .............. 128/203.12, 203.15, 128/203.18, 203.19, 203.21, 203.22, 203.23, 203.24; 222/390, 368, 321

[56] References Cited

U.S. PATENT DOCUMENTS

| | | |
|---|---|---|
| 2,581,182 | 1/1952 | Fields . |
| 4,046,146 | 9/1977 | Rosskamp et al. . |
| 4,274,403 | 6/1981 | Struve . |
| 4,524,769 | 6/1985 | Wetterlin et al. . |
| 4,543,345 | 8/1985 | Wetterlin et al. . |
| 4,565,302 | 1/1986 | Pfeiffer et al. .............. 222/321 |
| 4,627,432 | 12/1986 | Newell et al. . |
| 4,667,668 | 5/1987 | Wetterlin et al. . |
| 4,668,218 | 5/1987 | Virtanen .................... 604/58 |
| 4,805,811 | 2/1989 | Wetterlin .................... 222/337 |
| 4,811,731 | 3/1989 | Newell et al. . |
| 4,871,092 | 10/1989 | Maerte ...................... 222/321 |
| 4,907,583 | 3/1990 | Wetterlin et al. . |
| 5,033,463 | 7/1991 | Cocozza ................... 128/203.15 |

FOREIGN PATENT DOCUMENTS

| | | |
|---|---|---|
| 668771 | 8/1963 | Canada ...................... 128/205.12 |
| 0079478 | 5/1983 | European Pat. Off. . |
| 2041763 | 9/1980 | United Kingdom . |
| 2165159 | 4/1986 | United Kingdom . |

*Primary Examiner*—J. Reed Fisher
*Assistant Examiner*—Kimberly L. Asher
*Attorney, Agent, or Firm*—Robert A. Franks; John J. Maitner; Eric S. Dicker

[57] ABSTRACT

A powder dispenser assembly includes a container for holding a supply of powdered material, the container including a conduit extending therethrough; a metering plate rotatably mounted with respect to the container beneath the supply of powdered material for supplying the powdered material to the conduit, the metering plate including perforated areas therein, each adapted to hold one metered amount of the powdered material, and a first set of ratchet teeth; a blade assembly for scraping the powdered material into the perforated areas, the blade assembly being positioned between the supply of powdered material and the metering plate; a mouthpiece for enabling inhalation of the metered amount of powdered material from one selected perforated area through the conduit; a base rotatably mounted with the container; a spring plate for biasing the metering plate into biased contact with the blade assembly, the spring plate being non-rotatably mounted in the base and including a second set of ratchet teeth for engaging the first set of ratchet teeth to provide engagement between the spring plate and the metering plate such that rotation of the bas relative to the container causes rotation of the metering plate relative to the container, and spring fingers for biasing the second set of ratchet teeth into engagement with the first set of ratchet teeth and for biasing the metering plate into engagement with the blade assembly; and a rotation limiting mechanism for limiting rotation of the base relative to the container to an incremental angle of rotation.

4 Claims, 4 Drawing Sheets

DOSING DEVICE FOR ADMINISTERING METERED AMOUNTS OF POWDERED MEDICAMENTS TO PATIENTS

BACKGROUND OF THE INVENTION

The present invention relates generally to powder dispenser assemblies, and more particularly, is directed to a powder dispenser assembly used for inhalation of a metered dose of a powdered medicament.

When delivering medicaments, that is, pharmacologically active compounds in solid, micronized form, to the respiratory tract and to the lungs, careful attention to the accuracy of the dosage must be made, which can be as small as 0.1 mg. This is because such medicaments are often quite potent, and the administration of excessive amounts thereof could cause damage to the respiratory tract and to the lungs. In like manner, if the dosage that is delivered is too small, it will not serve its purpose.

It is also necessary that the particles that leave the dispenser assembly be within a particular range, since particles of the medicament which are too large may not enter the respiratory tract, but instead, will be deposited in the mouth and thence to the digestive tract. As an example, the particles can have a diameter of 5 $\mu$m or less.

Various devices have been used in order to dispense a metered dose of powdered medicament, including pressurized aerosol devices, nebulizing devices, pump inhalators and the like. With the concern over environmental issues, however, aerosol devices, which constitute a large part of the devices now on the market, are being shunned. Further, with aerosol devices, the medicament is dissolved or suspended in a liquid propellant mixture, and this further adds to the complexity of the devices.

In addition to the aforementioned types of dispenser assemblies, powder dispenser assemblies are also known. Studies have shown that there are virtually no significant differences in bronchodilator responses to medicinal substances administered either by powder dispensing devices or aerosol devices. Accordingly, there is now an ever-growing demand for powder dispensing devices which can dispense metered doses of powdered medicament. With such devices, the powder is dispensed with the start of inspiration following expiration so that there is no need to provide a synchronized release of medication with the start of inspiration to insure quality of the product under this use.

For example, U.S. Pat. No. 4,274,403 to Struve discloses an inhaler including a body having a dispensing head coupled thereto. The body includes a first storage chamber for storing a supply of powdered drugs therein and a second storage chamber for holding a desiccating agent. A dispensing cylinder is contained in a transverse bore in the dispensing head and is laterally movable from a first transverse position in which a diametrical bore is in alignment with a feed hole of the first storage chamber and a second transverse position in which the diametrical bore is out of alignment with the first storage chamber and communicates with the dispensing passageway of the nozzle of the dispensing head. In operation, the user inverts the inhaler such that the first storage chamber is positioned above the diametrical bore. In this position, the powdered drug therein falls into the diametrical bore and remains therein. Then, the user depresses the head of the dispensing cylinder against the action of a spring so as to move the diametrical bore out of alignment with the feed hole for the first storage chamber and into alignment with the dispensing passageway of the nozzle. The inhaler is then inverted back to the position in which the first storage chamber is positioned below the dispensing head, and the nozzle thereof is inserted in a nostril of the user so that upon inhalation, the powdered drug in the diametrical bore is nasally inhaled. To aid in such inhalation, a horizontally extending bore connects the diametrical bore or metering chamber to ambient atmosphere in the second transverse position.

However, in normal use, it is required that the inhaler be inverted so that the first storage chamber is above the dispensing head in order to dispense the powdered drug therefrom into the diametrical bore metering chamber, and then the inhaler must be reinverted to its original position in which the first storage chamber is below the dispensing head for the inhalation process. This becomes cumbersome in practice. In addition, the use of a dispensing cylinder having a single diametrical bore therein as the metering chamber is disadvantageous. This is because a single elongated diametrical bore of reduced cross-section provides some resistance to inhalation, particularly when the device is used by those persons having difficulty breathing and who cannot therefore provide the necessary suction. In addition, the use of such single diametrical bore with the air passageway extending substantially midway therein, may result in the powdered drug in the diametrical bore metering chamber, which is at a level below the intersection with the air passageway, remaining in the diametrical bore. As a result, the user may not inhale the entire metered amount in the diametrical bore metering chamber.

U.K. Patent No. 2,165,159 to Auvinent et al. discloses a dosing device having a fixed storage chamber for a medicinal powder, a mouthpiece and a venturi restriction between the mouthpiece and the storage chamber. A metering device is provided in the housing between the venturi restriction and the storage chamber and includes a rod having depressions therein for measuring the dose of the medicinal substance. The rod is rotatable to thereby deposit the medicinal powder in a depression thereof to the venture restriction. The device for rotating the rod is an indexing mechanism much like that of a ball-point pen. However, because of the cup-like arrangement of this patent, adhesion can occur along the walls of each depression, which is disadvantageous from a delivery viewpoint. See also European Patent Application No. 0079478 for a similar disclosure.

U.K. Patent No. 2,041,763 to Chiesi et al., the entire disclosure of which is incorporated herein by reference, discloses an inhaler for pulverulent medicinal substances, in which there is rotation of the housing parts relative to each other in order to obtain proper dosing and dispensing for inhalation through the nozzle. Specifically, there is a rotatable arrangement with the nozzle, the conduit connected to the nozzle and the storage chamber adjacent the conduit for storing an active compound to be dispensed by the inhalator. The bottom of the body which defines the storage chamber has two opposing arcuate dosing holes, each of which has a volume exactly corresponding to one dose of medicament. The tubular element which forms the conduit has a skirt corresponding to the length of the dosing holes for closing the dosing holes alternatively. Further, a dispensing disk provided with a dispensing hole is positioned immediately below the bottom such that the hole can be provided in registration with either of the dosing holes. The dispensing disk is secured to the bottom of the element which defines the conduit. In this regard, the skirt, conduit and dispensing disk move together as a unit in relation to the bottom containing the dosing holes. Immediately below the dispensing disk, there is provided a cavity communicating with the bottom of the conduit.

However, there is no dosing loading means for introducing the active compound from the storage chamber through the dosing holes. Rather, the medicament falls by gravity into the dosing holes. Accordingly, the device may not be suitable for use with micronized powder which requires dosage accuracy, since the micronized medicament will not fall by its own weight with any predictable accuracy into or out of the dosing holes, but rather, will stick together and stick to the walls of the chamber. Further, neither of the dosing holes is positioned across the conduit at any time. Rather, the dosing holes are always in surrounding relation to the conduit. As a result, the air flow to the user is somewhat tortuous, and some of the medicament may not be removed, causing dosage inaccuracy.

U.S. Pat. No. 4,524,769 to Wetterlin, the entire disclosure of which is incorporated herein by reference, attempts to cure the deficiencies of Chiesi et al. Specifically, this patent to Wetterlin, which is similar in many respects to Chiesi et al., includes a dosing unit that includes a storage chamber for holding the active compound, a perforated membrane rotatably positioned under the storage chamber and a holder for the membrane. Introduction of the active compound into the perforations in the perforated membrane is accomplished with elastic, spring-loaded scrapers, mounted in a holder in the storage chamber. With this arrangement, the membrane is movable between a first position where active compound is introduced by the scrapers in part of the area of the perforated membrane, and a second position where the part area of the loaded membrane has been inserted into the air conduit in the dosage inhalator. Thus, the active compound contained in the perforations is entrained at inhalation and brought through the nozzle to the respiratory tract and the lungs of the patient.

However, with this arrangement, a separate coil spring must be used to bias the scrapers into engagement with the perforated membrane, thereby complicating the construction and assembly of the device. The coil spring is interposed in the storage chamber between the casing and the scraper assembly. Alternatively, it is disclosed that the separate coil spring can be arranged so that the membrane is pressed against the scrapers, and thereby mounted in the base or maneuvering unit. In addition to the coil spring, Wetterlin uses spring loaded pins beneath the membrane to engage the ratcheted bottom of the membrane in order to provide distinct positions for the perforated membrane when it is advanced by the base or maneuvering unit. This, of course, further complicates the construction and assembly of the device. See also U.S. Pat. Nos. 4,907,583; 4,534,345; and 4,667,668, all to Wetterlin.

Other patents of related interest are U.S. Pat. No. 2,581,182 to Fields, European Patent Application No. 0079478 to Douglas, U.S. Pat. No. 4,046,146 to Rosskamp et al., U.S. Pat. No. 4,627,432 to Newell et al. and U.S. Pat. No. 4,811,731 to Newell et al.

OBJECTS AND SUMMARY OF THE INVENTION

Accordingly, it is an object of the present invention to provide a powder dispensing assembly that overcomes the problems with the aforementioned prior art.

It is another object of the present invention to provide a metered powder dispensing assembly that is activated by inhalation by the patient.

It is still another object of the present invention to provide a powder dispensing assembly that will dispense metered doses of powdered medicament to a patient.

It is yet another object of the present invention to provide a powder dispensing assembly that accurately measures the doses of powdered medicament to be delivered to the patient.

It is a further object of the present invention to provide a powder dispensing assembly that is greatly simplified in construction and assembly over the prior art.

It is still a further object of the present invention to provide a powder dispensing assembly having a one-piece molded spring plate that simultaneously provides positive engagement with the ratchet teeth of the metering plate to rotate the metering plate with respect to the container without the need for separate spring pins, ensures positive engagement of the blades with the upper surface of the metering plate without the need for a separate coil spring, and provides the necessary air draft by supplying air from primary air inlet ports.

In accordance with an aspect of the present invention, a powder dispenser assembly includes container means for holding a supply of powdered material to be dispensed, the container means including a conduit extending therethrough in displaced relation to the supply of powdered material, the conduit having first and second opposite ends; metering plate means for holding at least one metered amount of the powdered material, the metering plate means being rotatably mounted with respect to the container means beneath the supply of powdered material and adapted to be in fluid communication with the first end of the opening for supplying the powdered material thereto, the metering plate means including at least one perforated area therein, each perforated area adapted to hold one metered amount of the powdered material, and first ratchet means for enabling rotation of the metering plate means with respect to the container means; blade means for scraping the powdered material into the at least one perforated area, the blade means being positioned between the supply of powdered material and the metering plate means and being substantially fixed with respect to the container means; mouthpiece means for enabling inhalation of the metered amount of powdered material from one selected area in the metering plate means through the conduit in the container means, the mouthpiece means being in fluid communication with the second end of the opening; a base rotatably mounted with the container means; spring plate means for biasing the metering plate means into biased contact with the blade means, the spring plate means being non-rotatably mounted in the base and including fixation means for mounting the spring plate means in the base in a non-rotatable manner, second ratchet means for engaging the first ratchet means to provide engagement between the spring plate means and the metering plate means such that rotation of the base relative to the container means causes rotation of the metering plate means relative to the container means, the second ratchet means being fixed to the fixation means, and spring finger means for biasing the second ratchet means of the spring plate means into engagement with the first ratchet means of the metering plate means and for biasing the metering plate means into engagement with the blade means, said spring finger means being fixed to the fixation means and engaging the base; and rotation limiting means for limiting rotation of the base relative to the container means to an incremental angle of rotation.

The above and other objects, features and advantages of the invention will become readily apparent from the following detailed description thereof which is to be read in connection with the accompanying drawings.

DETAILED DESCRIPTION OF A PREFERRED EMBODIMENT

Figures 1, 2:
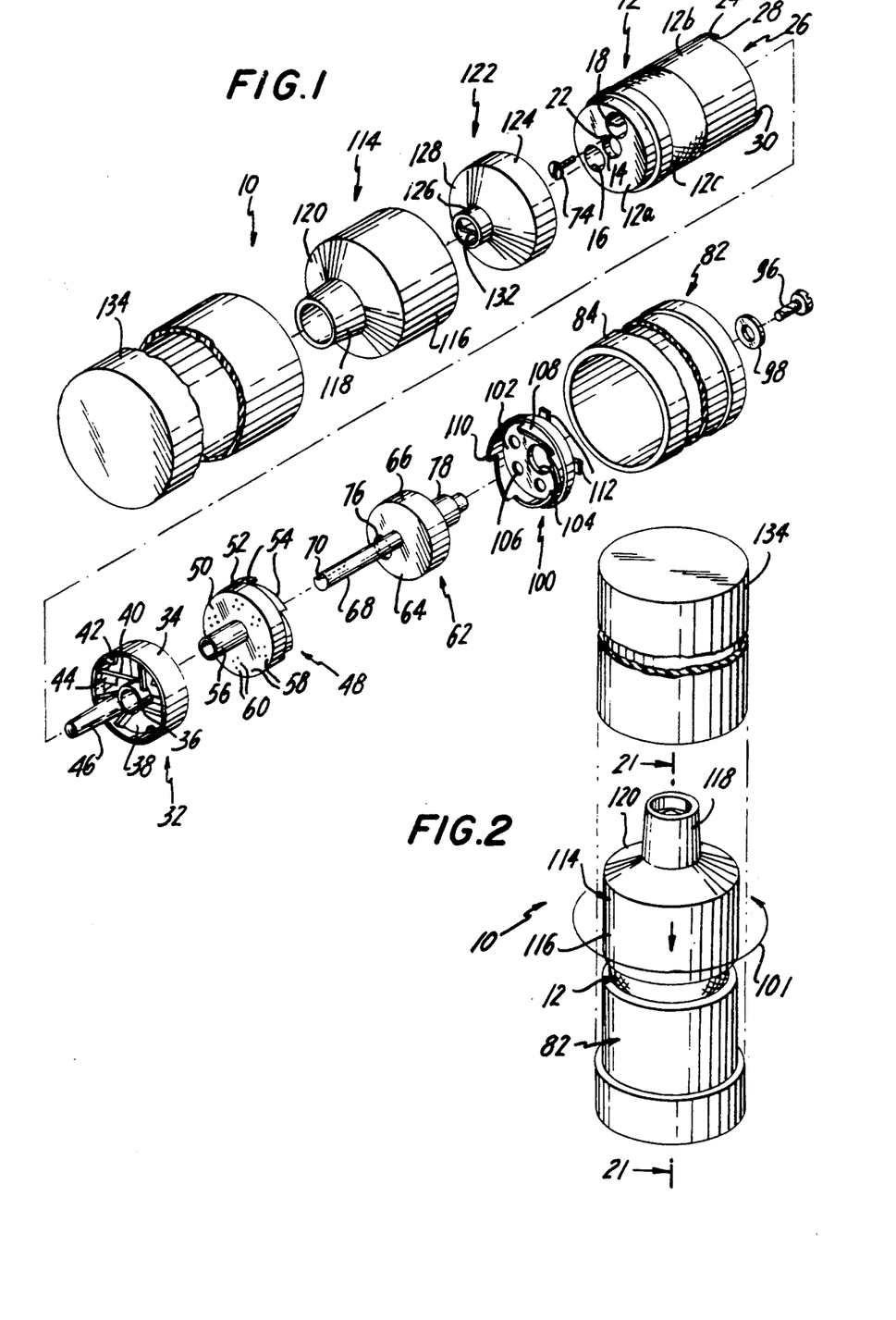
FIG. 1 is a blown-apart, perspective view of the powder dispensing assembly according to the present invention.
FIG. 2 is an assembled perspective view of the dispensing assembly of FIG. 1, with the overcap removed.
Figure 3:
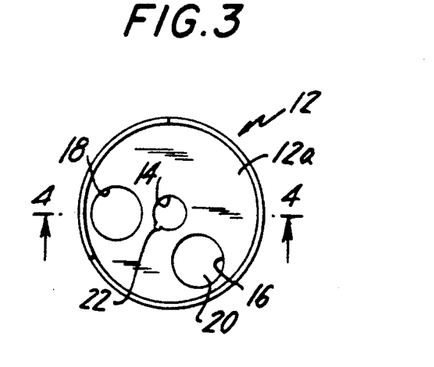
FIG. 3 is a top plan view of the container of the powder dispensing assembly of FIG. 1.
Figure 4:
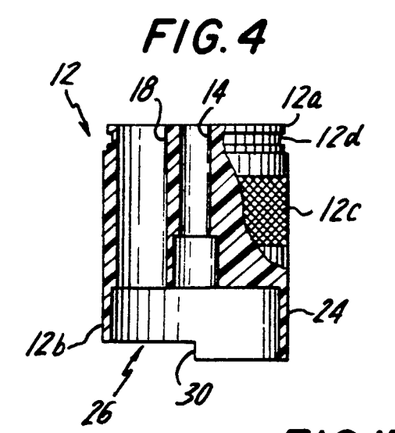
FIG. 4 is a cross-sectional view of the container of FIG. 3, taken along line 4—4 thereof.

Referring to the drawings in detail, and initially to FIGS. 1, 3 and 4 thereof, a device 10 according to the present invention for administering a medicinal powder by inhalation, includes a main body or container 12 of a generally solid cylindrical configuration having an upper or delivery end 12a, a lower or metering end 12b and a knurled or roughened outer surface 12c. Container 12 has a central bore 14 extending therethrough in the axial direction of container 12, as well as two additional bores 16 and 18 extending therethrough in the axial direction and offset from the center line thereof which extends through central bore 14. Bore 16 constitutes an inhalation conduit through which the patient inhales a metered dose of the medicament, while bore 18 constitutes the storage chamber for the supply of medicament to be metered out. In this regard, bore 18 is closed off at the upper or mouthpiece end by a plug 20 after the medicament is deposited therein, to prevent inhalation of the medicament directly from bore 18. Further, a hemispherical threaded groove 22 is cut into delivery end 12a of container 12 in as a radially outward extension of and in communication with central bore 14.

Container 12 further includes an annular flange 24 extending integrally from the outer wall of metering end 12b thereof, with annular flange 24 being partially cutaway for an arcuate angle of approximately 100 degrees at 26, so as to define first and second limit end walls 28 and 30, the reason for which will become apparent from the discussion which follows. Container 12 is preferably of a one-piece molded plastic construction.

As shown best in FIGS. 1 and 5-7, device 10 further includes a blade assembly 32 comprised of an outer annular wall 34 and an inner concentric annular wall 36 connected to outer annular wall 34 by a solid plate-like area 38 extending about a 120 degree arc and by a plurality of vanes 40. Inner annular wall 36 defines a central opening 37. In the present example, three vanes 40 are shown, although this number may vary. It will also be appreciated that vanes 40 are not purely radially directed, but have a tangential component in their direction. Outer annular wall 34 has an outer diameter that is only slightly smaller than the inner diameter of annular flange 24 of container 12 so that outer annular wall 34 can fit within annular flange 24, preferably with a friction fit. However, it will be appreciated that when blade assembly 32 is positioned within annular flange 24, the lower edge of annular wall is even with or above the lower edge of cut-away portion 26 of annular flange 24 so as not to interfere with the operation of limit end walls 28 and 30, as will be described hereinafter.

Figure 5:
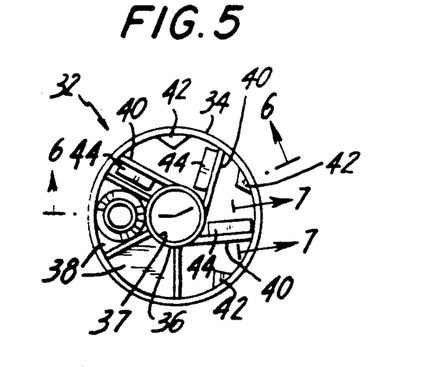
FIG. 5 is a top plan view of the blade assembly of the powder dispensing assembly of FIG. 1.
Figure 6:
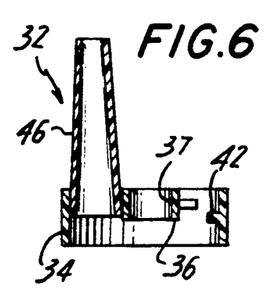
FIG. 6 is a cross-sectional view of the blade assembly of FIG. 5, taken along line 6—6 thereof.
Figure 7:
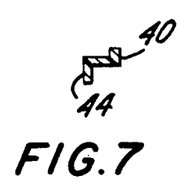
FIG. 7 is a cross-sectional view of one blade of the blade assembly of FIG. 5, taken along line 7—7 thereof.

Triangular projections 42 extend from the inner surface of outer annular wall 34 in each open area defined between solid area 38 and vanes 40, to help break apart any particles of the powdered material that have stuck together. Further, and in accordance with an important aspect of the present invention, L-shaped blades 44 are integrally formed with each vane 40 and extend downwardly therefrom away from container 12. Preferably, the portion of each blade 44 in contact with the metering plate (described hereinafter), contacts the metering plate at an angle other than 90°.

Finally, a hollow tubular member 46 is mounted to solid plate-like area 38 and extends within bore 16 which defines the inhalation conduit to prevent rotation of blade assembly 32 with respect to container 12, while still permitting inhalation through inhalation conduit 16. Alternatively, hollow tubular member 46 can be eliminated. In such case, outer annular wall 34 would fit within annular flange 24 with a press or friction fit so as to prevent rotation of blade assembly 32 with respect to container 12. The entire blade assembly 32 is preferably of a one-piece molded plastic construction.

Figure 8:
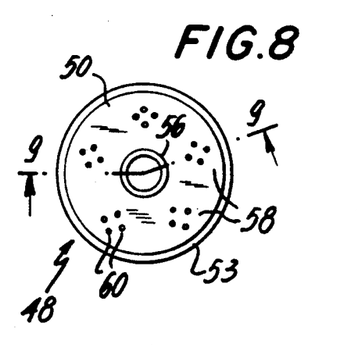
FIG. 8 is top plan view of the metering plate of the powder dispensing assembly of FIG. 1.
Figure 9:
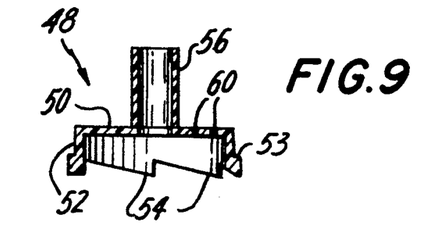
FIG. 9 is a cross-sectional view of the metering plate of FIG. 8, taken along line 9—9 thereof.

Referring now to FIGS. 1, 8 and 9, device 10 further includes a perforated metering plate 48 comprised of a circular flat plate portion 50 having a downturned annular lip 52 at the periphery thereof, with a plurality of ratchet teeth 54 formed at the lower end of lip 52. Although five equally spaced ratchet teeth 54 are shown, it will be appreciated that this number can vary within the scope of the present invention. However, the angular extent of each ratchet tooth 54 will be preferably be less than angular extent of cut-away portion 26 of annular flange 24. The outer diameter of annular lip 52 is less than the inner diameter of outer annular wall 34 of blade assembly 32 so that metering plate 48 fits within outer annular wall 34 and can rotate with respect to blade assembly 32 and container 12. In this regard, annular lip 52 is formed with a lower annular shoulder 53 of greater diameter against which the lower edge of outer annular wall 34 can abut. Further, the lowest edge 54a of each tooth 54 extends substantially to the same level as the lower edge of annular flange 24 of container 12.

A central tubular member 56 is formed on and extends through circular flat plate portion 50. Central tubular member 56 seats through central opening 37 of blade assembly 32 to provide rotation of metering plate 48 with respect to blade assembly 32 and container 12.

More importantly, circular flat plate portion 50 of metering plate 32 includes a plurality of perforated areas 58 extending circumferentially and equiangularly therearound, each for holding a metered amount of the powdered material. Although five such areas 58 are shown, this number may vary. However, the number of perforated areas 58 will correspond to the number of ratchet teeth 54 and will generally be aligned with the leading edge of each respective ratchet tooth 54. Each perforated area 58 is preferably constituted by a plurality of, for example four, small holes 60 which are adapted to hold a predetermined amount of powdered material. Holes 60 preferably have a frusto-conical construction, as shown in FIG. 9, in the manner taught by Wetterlin '769. The entire metering blade 48 is preferably of a one-piece molded plastic construction.

Thus, with the assembly so far described, the powdered medicament falls through the lower open end of bore 18 which defines the storage chamber, and through the open areas between vanes 40 onto the upper surface of flat plate portion 50 of metering plate 48. As metering plate 48 is rotated with respect to blade assembly 32, blades 44 which are in contact with the upper surface of flat plate portion 50, force the powdered medicament into holes 60. Then, when a perforated area 58 of metering plate 48 is rotated to a position below inhalation conduit 16, inhalation by the user results in withdrawal of the powdered medicament from holes 60 in the particular perforated area 58 therebelow, into inhalation conduit 16, and then to the patient. As a result, the patient gets an exact, metered amount of medicament.

Figure 10:
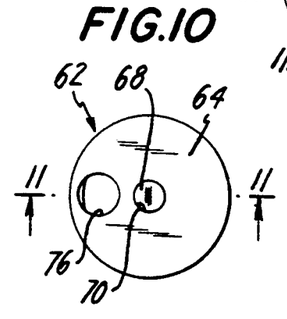
FIG. 10 is a top plan view of the platform member of the powder dispensing assembly of FIG. 1.
Figure 11:
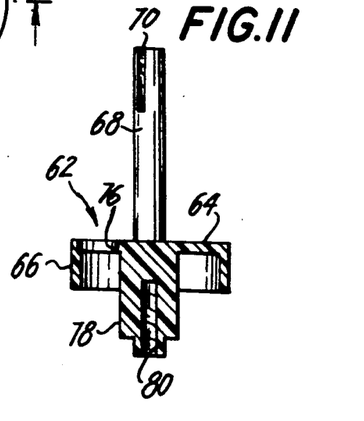
FIG. 11 is a cross-sectional view of the platform member of FIG. 10, taken along line 11—11 thereof.

As shown best in FIGS. 1, 10 and 11, device 10 further includes a platform member 62 positioned on the opposite side of metering plate 48 from blade assembly 32, in order to prevent the medicament deposited into holes 60 from falling therethrough. Specifically, platform member 62 includes a backing disk portion 64 having an outer diameter less than the inner diameter of annular lip 52, but sufficiently great to cover perforated areas 58. In this manner, when blades 44 push the medicament into holes 60, disk portion 64 prevents the medicament from falling through holes 60 and also assures that the medicament fills the entire height of holes 60.

Figure 22:
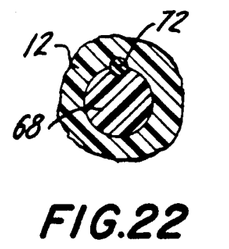
FIG. 22 is a cross-sectional view of the powder dispensing assembly of FIG. 21, taken along line 22—22 thereof.
Figure 23:
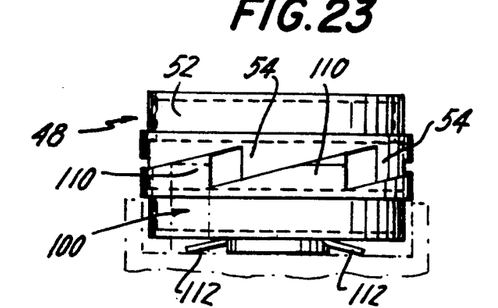
FIG. 23 is an elevational view showing the metering plate and spring plate out of meshing engagement.

Platform member 62 further includes an annular lip 66 extending down (away from container 12) from the peripheral edge of disk portion 64. A central upper shaft 68 is formed integrally at the upper surface of disk portion 64, and extends through central tubular member 56 of metering plate 48 and central opening 37 of container 12. The upper end of shaft 68 has a hemispherical threaded groove 70 which, together with hemispherical threaded groove 22, forms a threaded opening 72 at delivery end 12a of container 12, as best shown in FIG. 22. A set screw 74 is threaded into threaded opening 72, fixing shaft 68, and thereby platform member 62, in position with respect to container 12.

The reason that platform member 62 is fixed in position with respect to container 12 is that disk portion 64 thereof has a draw hole 76 therein through which air can be drawn through conduit 16, in order to aid in the removal of the powdered medicament in holes 60 of the perforated area 58 positioned under conduit 16 during inhalation. In accordance with an important aspect of the present invention, draw hole 76 is fixed in position with respect to conduit 16 because of the fixed arrangement of platform member 62 with container 12 by means of set screw 74.

In addition, platform member 62 includes a lower centrally located tubular member 78 having internal threads 80 therein, the reason for which will be apparent from the discussion hereinafter. The entire platform member 32 is preferably of a one-piece molded plastic construction.

Referring now to FIGS. 1, 2, 12 and 13, device 10 further includes a base 82 rotatably mounted with container 12. Specifically, base 82 is formed with a cylindrical wall 84 having an inner diameter slightly greater than the outer diameter of container 12 so as to receive metering end 12b thereof for rotation of base 82 with respect to container 12. The lower end of cylindrical wall 84 is closed off by a bottom wall 86 having a central aperture 88 and a plurality of primary air inlet ports 89 therein. Bottom wall 86 is also formed with an upstanding pin 90 extending in the axial direction of cylindrical wall 84 and positioned between cylindrical wall 84 and central aperture 88.

Figure 12:
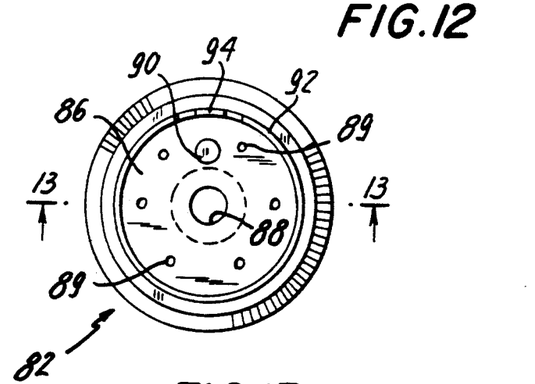
FIG. 12 is a top plan view of the base of the powder dispenser assembly of FIG. 1.
Figure 13:
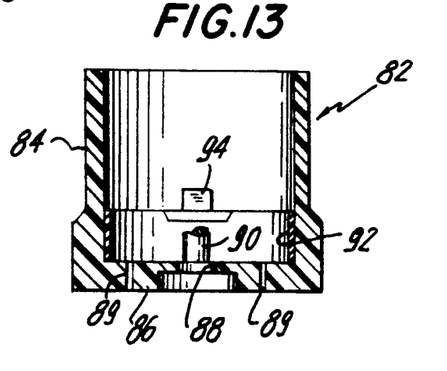
FIG. 13 is a cross-sectional view of the base of FIG. 12, taken along line 13—13 thereof.

Finally, the inner surface of cylindrical wall 84 is formed with a lower annular ridge 92 which limits the downward travel of container 12 therein. In other words, the lower edge of annular flange 24 of container 12 rests upon annular ridge 92 when container 12 seats within base 82. In addition, annular ridge 92 includes an upwardly projecting stop 94 which seats within cut-away portion 26 of annular flange 24 when annular flange 24 rests upon ridge 92. In this manner, first and second limit end walls 28 and 30 of annular flange 24 hit against stop 94 when container 12 is rotated with respect to base 82 to limit the extent of rotation of container with respect to base 82, to a predetermined angular extent corresponding to one ratchet tooth 54. The entire base 82 is preferably of a one-piece molded plastic construction.

Container 12 has its axial position fixed to base 82, while permitting rotational movement between these elements. In this regard, when container 12 seats within base 82, lower centrally located tubular member 78 of platform member 62 extends partially within central aperture 88. A screw 96 is inserted through a washer 98 and then through central aperture 88 so that screw 96 threadedly engages internal threads 80 of lower centrally located tubular member 78 to axially lock container 12 to base 82, while permitting rotation with respect thereto.

In accordance with an important aspect of the present invention, and as best shown in FIGS. 1 and 14–16, a spring plate 100 is interposed between platform member 62 and base 82, for biasing metering plate 48 into biased contact with blades 44 of blade assembly 32. Spring plate 100 is non-rotatably mounted in base 82. In this regard, spring plate 100 includes a fixation disk 102 having an outer diameter less than that of annular ridge 92 so as to seat in base 82 within the confines of annular ridge 92. Fixation disk 102 is provided with a central aperture 104 through which lower centrally located tubular member 78 of platform member 62 extends, and a plurality of equiangularly, circumferentially spaced holes 106, any one of which receives upstanding pin 90 in order to prevent rotation of fixation disk 102 within base 82. As will be appreciated from the discussion hereinafter, holes 106 serve the dual purpose of supplying air from primary air inlet ports 89 to conduit 16, as well as non-rotatably positioning fixation disk 102 within base 82.

Figure 14:
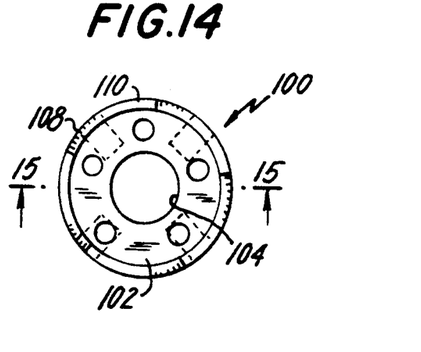
FIG. 14 is a top plan view of the spring plate of the powder dispenser assembly of FIG. 1.
Figure 15:
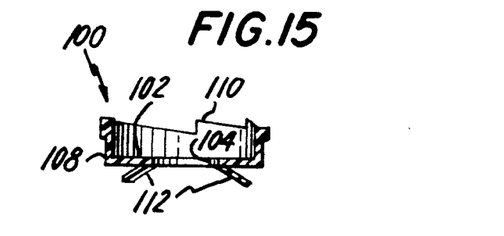
FIG. 15 is a cross-sectional view of the spring plate of FIG. 14, taken along line 15—15 thereof.
Figure 16:
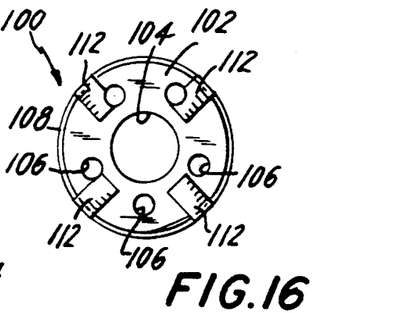
FIG. 16 is a bottom plan view of the spring plate of FIG. 14.
Figure 17:
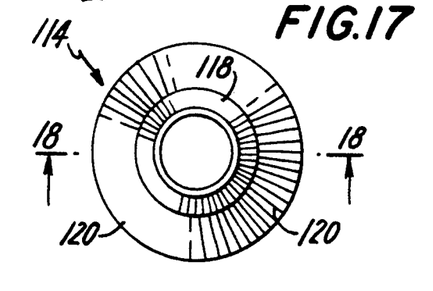
FIG. 17 is a top plan view of the mouthpiece of the powder dispensing assembly of FIG. 1.
Figure 18:
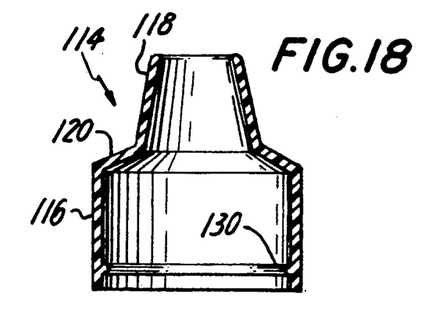
FIG. 18 is a cross-sectional view of the mouthpiece of FIG. 17.
Figure 19:
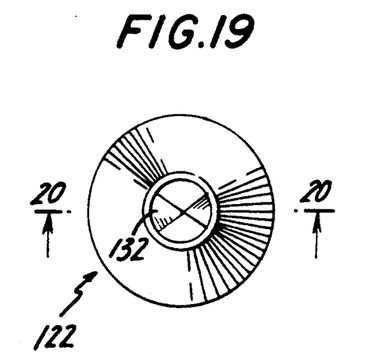
FIG. 19 is a top plan view of the mouthpiece insert of the powder dispensing assembly of FIG. 1.
Figure 20:
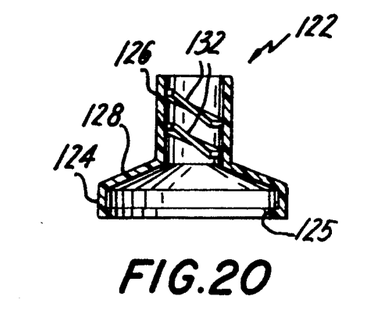
FIG. 20 is a cross-sectional view of the mouthpiece insert of FIG. 19.

Spring plate 100 also includes an upstanding annular lip 108 having a plurality of ratchet teeth 110 for engaging ratchet teeth 54, to provide engagement between spring plate 100 and metering plate 48 such that rotation of base 82 relative to container 12 causes rotation of metering plate 48 relative to container 12. Preferably, the number of ratchet teeth 110 is the same as the number of ratchet teeth 54 in order to obtain a strong and positive engagement between spring plate 100 and metering plate 48.

Spring plate 100 also includes a plurality of spring fingers 112 fixed to fixation disk 102 and engaging bottom wall 86 of base 82 to bias ratchet teeth 110 of spring plate 100 into engagement with ratchet teeth 54 of metering plate 48.

The entire spring plate 100 is preferably of a one-piece molded plastic construction.

It will therefore be appreciated that spring plate 100 provides a multitude of functions. First, ratchet teeth 110 provide positive engagement with ratchet teeth 54 to enable rotation of metering plate 48 with respect to container 12 when base 82 is rotated with respect to container 12, without the need for the spring pins of U.S. Pat. No. 4,524,769 to Wetterlin. Second, the use of spring fingers 112 ensures positive engagement of ratchet teeth 54 and 110 with each other without the need for the spring pins of U.S. Pat. No. 4,524,769 to Wetterlin. Third, spring fingers 112 ensure positive engagement of blades 44 with the upper surface of flat plate portion 50 of metering plate 48, without the need for the coil spring of U.S. Pat. No. 4,524,769 to Wetterlin. Fourth, holes 106 provide that spring plate 100 is axially movable (due to spring fingers 112), yet not rotatable with respect to base 82. Fifth, holes 106 provide the necessary air draft by supplying air from primary air inlet ports 89 to conduit 16.

Figure 21:
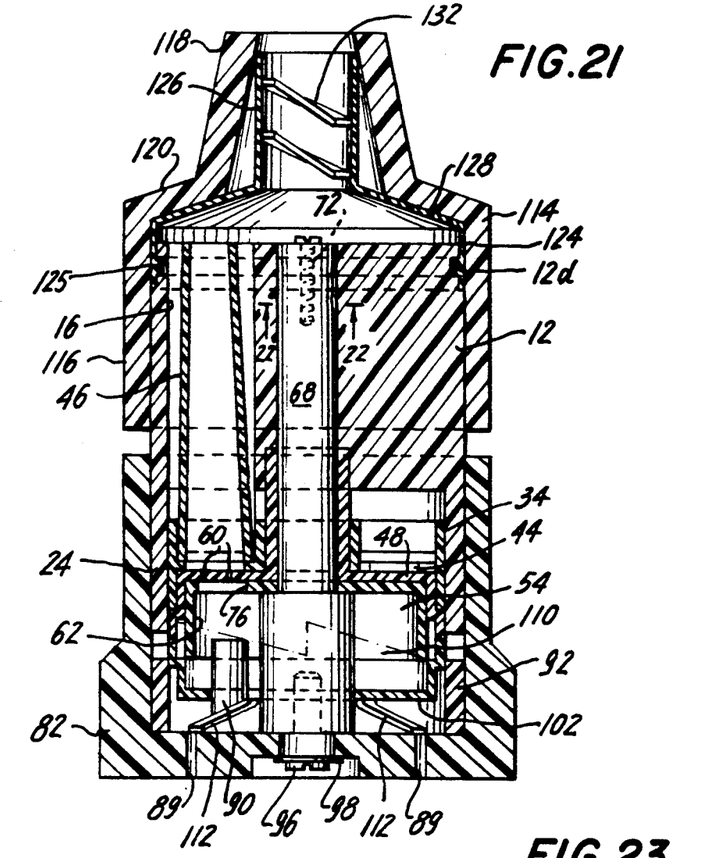
FIG. 21 is a cross-sectional view of the powder dispensing assembly of FIG. 2, taken along line 21—21 thereof.

With the arrangement thus far described, and as best shown in FIG. 21, spring plate 100 axially biases the upper surface of disk portion 64 of platform member 62 into engagement with the lower surface of flat plate portion 50 of metering plate 48 so as to prevent the powdered material from falling through holes 60. At the same time, spring plate 100 results in the upper surface of flat plate portion 50 of metering plate 48 being biased into engagement with blades 44 of blade assembly 32 so that when metering plate 48 is rotated with respect to blade assembly 32, blades 44 scrape the powdered material into holes 60 so as to accurately fill the same.

Figure 24:
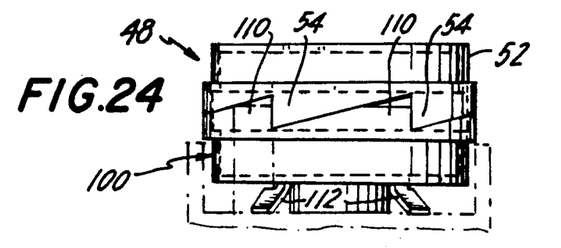
FIG. 24 is an elevational view showing the metering plate and spring plate in meshing engagement.

At the same time, spring plate 100, during such biasing action, forces ratchet teeth 110 into meshing engagement with ratchet teeth 54, as shown in FIGS. 21 and 24. In this manner, when container 12 is rotated with respect to base 82 (in the direction of arrow 101 in FIG. 2) by the user in a first direction, metering plate 48 is caused to rotate with base 82. However, it will be appreciated that, in the assembly thus far described, upwardly projecting stop 94 is positioned within cut-away portion 26. Accordingly, base 82 is restricted in its rotation to a small angular range defined by stop 94 hitting against second limit end wall 30 of cut-away portion 26. This angular extent is equal to or slightly greater than the angular extent of each ratchet tooth 54.

During such rotational movement of metering plate 48 with respect to container 12, blades 44 force powdered material into holes 60 in the perforated areas 58 immediately below blades 44, so as to fill holes 60. At the same time, holes 60 in the already filled perforated area 58 following blades 44 are moved to a position immediately below conduit 16. At this position, draw hole 76 is in line with conduit 16 so that, by way of inhalation, the exact metered amount of powdered material is inhaled.

Thereafter, to receive a further dosage, container 12 must be rotated back to its original position with respect to body 82, that is, in the opposite rotational direction, since it cannot rotate further in the same direction with respect thereto. During the return rotational movement, ratchet teeth 110 ride over ratchet teeth 54, that is, ratchet teeth 54 and 110 are no longer in meshing or driving engagement, as shown in FIG. 23. During such riding over movement, spring fingers 112 are depressed in the axial direction of device 10, and thereby move in the radially outward direction, to permit such riding over movement. Then, before stop 94 hits against first limit end wall 28 of cut-away portion 26, teeth 54 and 110 are again in meshing engagement. Stop 94 thereafter hits against first limit end wall 28 to limit further reverse rotation of container 12 with respect to base 82. Thereafter, the steps can be repeated to provide another dose below conduit 16.

As shown in FIGS. 1, 2, 17 and 18, device 10 further includes a mouthpiece 114 having a securement portion 116 in the form of a cylinder which fits with a friction fit over the upper portion of the outer surface of container 12 in spaced relation to base 82 which fits over the lower portion of the outer surface of container 12. Mouthpiece 114 further includes a frusto-conical inhalation portion 118 having its large base diameter much less than the diameter of cylindrical securement portion 116, and connected thereto by means of a frusto-conical connecting portion 120. The entire mouthpiece 114 is preferably of a one-piece molded plastic construction.

Thus, after providing the initial rotation in the direction of arrow 101, it is only necessary for the user to place his mouth on the upper smaller base opening of inhalation portion 118 and inhale, in order to receive the exact metered amount of powdered medicament. It will be appreciated that secondary air axially directed channels (not shown) can be formed on the outer surface of container 12 beneath mouthpiece 114 to provide secondary air, if necessary.

In order to prevent aggregation of the particles from holes 60 to the patient, a mouthpiece insert 122 is provided in mouthpiece 114. Mouthpiece insert 122 is of similar, but slightly smaller, shape to mouthpiece 114, and thereby includes a cylindrical portion 124 which fits within securement portion 116, a small cylindrical deflecting portion 126 which fits within inhalation portion 118, and a frusto-conical connecting portion 128 which connects cylindrical portions 124 and 126 together, and which fits within frusto-conical connecting portion 120. In order to prevent escape of mouthpiece insert 122 from mouthpiece 114, the inner surface of securement portion 116 is formed at the lower end thereof With an annular bead 130 which restricts the lower inner diameter of securement portion 116 to a lesser diameter than the outer diameter of cylindrical portion 124 of mouthpiece insert 122. Further, cylindrical portion 124 has a lower inner annular bead 125 which mates with an annular recess 12d at upper end 12a of container 12.

More importantly, deflecting portion 126 of mouthpiece insert 122 includes a plurality of, for example two, helical vanes 132 secured to the inner surface thereof. As in U.S. Pat. No. 4,907,583 to Wetterlin, the entire disclosure of which is incorporated herein by reference, helical vanes 132 deflect the powder particles so as to dash the same against the inner wall of deflecting portion 126 by centrifugal force, whereby large particles or particle aggregates are ground into small particles, and also, the particles collide with each other which results in a mutual grinding action between the particles. The entire mouthpiece insert 122 is preferably of a one-piece molded plastic construction.

Lastly, as shown in FIG. 2, device 10 includes a cylindrical cup-shaped overcap 134 which fits over mouthpiece 114 to close off the open end thereof when not in use. Overcap 134 fits thereon with a friction fit, and can easily be removed by the user.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention as defined by the appended claims.

What is claimed is:

1. A powder dispenser assembly comprising:
    container means for holding a supply of powdered material to be dispensed, said container means including a conduit extending therethrough in displaced relation to said supply of powdered material, said conduit having first and second opposite ends;
    metering plate means for holding at least one metered amount of said powdered material, said metering plate means being rotatably mounted with respect to said container means beneath said supply of powdered material and in fluid communication with the first end of said conduit for supplying said powdered material thereto, said metering plate means including:
        i) at least one perforated area therein, each said perforated area holding one said metered amount of said powdered material, and
        ii) first ratchet means for rotation of said metering plate means with respect to said container means;
    blade means for scraping said powdered material into said at least one perforated area, said blade means being positioned between said supply of powdered material and said metering plate means and being substantially fixed with respect to said container means;
    mouthpiece means for inhalation of said metered amount of powdered material from one selected perforated area in said metering plate means through the conduit in said container means, said mouthpiece means being in fluid communication with said second end of said conduit;
    a base rotatably mounted with respect to said container means;
    spring plate means for biasing said metering plate means into biased contact with said blade means, said spring plate means being non-rotatably mounted in said base and including:
        i) fixation means including a disk having a plurality of holes therein, for mounting said spring plate means in said base in a non-rotatable manner by engagement of at least one of said holes with pin means provided in said base,
        ii) second ratchet means for engaging said first ratchet means to provide engagement between said spring plate means and said metering plate means such that rotation of said base relative to said container means causes rotation of said metering plate means relative to said container means, said second ratchet means being fixed to said fixation means, and
        iii) spring finger means for biasing said second ratchet means of said spring plate means into engagement with said first ratchet means of said metering plate means and for biasing the metering plate means into engagement with the blade means, said spring finger means being fixed to said fixation means and engaging said base;
    rotation limiting means for limiting rotation of said base relative to said container means to an incremental angle of rotation; and
    said base being provided with a plurality of holes for supplying primary draft air through said plurality of holes in said disk to said conduit of said container means.

2. A powder dispenser assembly comprising:
    container means for holding a supply of powdered material to be dispensed, said container means including a conduit extending therethrough in displaced relation to said supply of powdered material, said conduit having first and second opposite ends;
    metering plate means for holding at least one metered amount of said powdered material, said metering plate means being rotatably mounted with respect to said container means beneath said supply of powdered material and in fluid communication with the first end of said conduit for supplying said powdered material thereto, said metering plate means including:

i) a flat plate portion,
ii) a peripheral lip extending perpendicularly about said flat plate portion,
iii) at least one perforated area in said flat plate portion, each said perforated area holding one said metered amount of said powdered material, each said perforated area of said metering plate means including a plurality of holes in said metering plate means, and
iv) first ratchet means for rotation of said metering plate means with respect to said container means, said first ratchet means including a plurality of ratchet teeth formed at a lower edge of said peripheral lip;

blade means for scraping said powdered material into said at least one perforated area, said blade means being positioned between said supply of powdered material and said metering plate means and being substantially fixed with respect to said container means;

platform means for preventing said powdered material deposited into said at least one perforated area from falling therethrough, said platform means being positioned below said metering plate means;

mouthpiece means for inhalation of said metered amount of powdered material from one selected perforated area in said metering plate means through the conduit in said container means, said mouthpiece means being in fluid communication with said second end of said conduit;

a base rotatably mounted with respect to said container means, said base including a pin therein;

spring plate means for biasing said metering plate means into biased contact with said blade means, said spring plate means being non-rotatably mounted in said base and including:
  i) fixation means for mounting said spring plate means in said base in a non-rotatable manner, said fixation means including a disk having a plurality of holes therein, at least one hole for receiving the pin of the base to mount said spring plate means in said base in a non-rotatable manner,
  ii) an annular lip formed at the periphery of said disk of said fixation means, said annular lip having an upper end,
  iii) second ratchet means for engaging said first ratchet means to provide engagement between said spring plate means and said metering plate means such that rotation of said base relative to said container means causes rotation of said metering plate means relative to said container means, said second ratchet means including a plurality of ratchet teeth formed at an upper edge of said annular lip for engaging the plurality of ratchet teeth formed at a lower edge of said peripheral lip of said metering plate means, and
  iv) spring finger means for biasing said second ratchet means of said spring plate means into engagement with said first ratchet means of said metering plate means and for biasing the metering plate means into engagement with the blade means, said spring finger means being fixed to said disk of said fixation means and engaging said base;

rotation limiting means for limiting rotation of said base relative to said container means to an incremental angle of rotation; and said base being provided with a plurality of holes for supplying primary draft air through said plurality of holes in said disk to said conduit of said container means.

3. A powder dispenser assembly comprising:

container means for holding a supply of powdered material to be dispensed, said container means including a conduit extending therethrough in displaced relation to said supply of powdered material, said conduit having first and second opposite ends;

metering plate means for holding at least one metered amount of said powdered material, said metering plate means being rotatably mounted with respect to said container means beneath said supply of powdered material and in fluid communication with the first end of said conduit for supplying said powdered material thereto, said metering plate means including:
  i) at least one perforated area therein, each said perforated area holding one said metered amount of said powdered material, and
  ii) first ratchet means for rotation of said metering plate means with respect to said container means;

platform means positioned below said metering plate means for preventing said powdered material deposited into said at least one perforated area from falling therethrough, said platform means including a plate for preventing the powdered material from falling through said at least one perforated area;

blade means for scraping said powdered material into said at least one perforated area, said blade means being positioned between said supply of powdered material and said metering plate means and being substantially fixed with respect to said container means;

mouthpiece means for inhalation of said metered amount of powdered material from one selected perforated area in said metering plate means through the conduit in said container means, said mouthpiece means being in fluid communication with said second end of said conduit;

a base rotatably mounted with respect to said container means and including a central aperture;

spring plate means for biasing said metering plate means into biased contact with said blade means, said spring plate means being non-rotatably mounted in said base and including:
  i) fixation means for mounting said spring plate means in said base in a non-rotatable manner,
  ii) second ratchet means for engaging said first ratchet means to provide engagement between said spring plate means and said metering plate means such that rotation of said base relative to said container means causes rotation of said metering plate means relative to said container means, said second ratchet means being fixed to said fixation means, and
  iii) spring finger means for biasing said second ratchet means of said spring plate means into engagement with said first ratchet means of said metering plate means and for biasing the metering plate means into engagement with the blade means, said spring finger means being fixed to said fixation means and engaging said base; and rotation limiting means for limiting rotation of said base relative to said container means to an incremental angle of rotation; and said base including means for axially fixing said container means to said base, while permitting relative rotation therebetween; said means for axially fixing including a tubular member extending from said platform means plate into alignment with said central aperture, and screw means extending through said central aperture for threadedly engaging said tubular member.

4. A powder dispenser assembly comprising:

container means for holding a supply of powdered material to be dispensed, said container means including a conduit extending therethrough in displaced relation to said supply of powdered material, said conduit having first and second opposite ends;

metering plate means for holding at least one metered amount of said powdered material, said metering plate means being rotatably mounted with respect to said container means beneath said supply of powdered material and in fluid communication with the first end of said conduit for supplying said powdered material thereto, said metering plate means including:
i) a flat plate portion,
ii) a peripheral lip extending perpendicularly about said flat plate portion,
iii) at least one perforated area in said flat plate portion, each said perforated area holding one said metered amount of said powdered material, each said perforated area of said metering plate means including a plurality of holes in said metering plate means, and
iv) first ratchet means for rotation of said metering plate means with respect to said container means, said first ratchet means including a plurality of ratchet teeth formed at a lower edge of said peripheral lip;

blade means for scraping said powdered material into said at least one perforated area, said blade means being positioned between said supply of powdered material and said metering plate means and being substantially fixed with respect to said container means;

platform means including a plate for preventing said powdered material deposited into said at least one perforated area from falling therethrough, said platform means being positioned below said metering plate means;

mouthpiece means for inhalation of said metered amount of powdered material from one selected perforated area in said metering plate means through the conduit in said container means, said mouthpiece means being in fluid communication with said second end of said conduit;

a base rotatably mounted with respect to said container means provided with a central aperture, said base including a pin therein;

spring plate means for biasing said metering plate means into biased contact with said blade means, said spring plate means being non-rotatably mounted in said base and including:
i) fixation means for mounting said spring plate means in said base in a non-rotatable manner, said fixation means including a disk having at least one hole therein for receiving the pin of the base to mount said spring plate means in said base in a non-rotatable manner,
ii) an annular lip formed at the periphery of said disk of said fixation means, said annular lip having an upper end,
iii) second ratchet means for engaging said first ratchet means to provide engagement between said spring plate means and said metering plate means such that rotation of said base relative to said container means causes rotation of said metering plate means relative to said container means, said second ratchet means including a plurality of ratchet teeth formed at an upper edge of said annular lip for engaging the plurality of ratchet teeth formed at a lower edge of said peripheral lip of said metering plate means, and
iv) spring finger means for biasing said second ratchet means of said spring plate means into engagement with said first ratchet means of said metering plate means and for biasing the metering plate means into engagement with the blade means, said spring finger means being fixed to said disk of said fixation means and engaging said base;

rotation limiting means for limiting rotation of said base relative to said container means to an incremental angle of rotation; and said base including means for axially fixing said container means to said base, while permitting relative rotation therebetween, said means for axially fixing including a tubular member extending from said platform means plate into alignment with said central aperture, and screw means extending through said central aperture for threadedly engaging said tubular member.

* * * * *